(12) United States Patent
Ortiz

(10) Patent No.: US 7,632,285 B2
(45) Date of Patent: *Dec. 15, 2009

(54) SHEATH FOR ENABLING INSERTION AND EXTRACTION OF ANASTOMOTIC RING APPLIER

(75) Inventor: Mark S. Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 440 days.

This patent is subject to a terminal disclaimer.

(21) Appl. No.: 11/120,824

(22) Filed: May 3, 2005

(65) Prior Publication Data

US 2006/0253133 A1 Nov. 9, 2006

(51) Int. Cl.
*A61B 17/10* (2006.01)
(52) U.S. Cl. .................. 606/142; 606/108; 606/153
(58) Field of Classification Search .................. 606/153, 606/108, 194, 142; 623/1.11, 1.23
See application file for complete search history.

(56) References Cited

U.S. PATENT DOCUMENTS

| | | | |
|---|---|---|---|
| 5,443,477 A * | 8/1995 | Marin et al. | 606/198 |
| 5,855,312 A | 1/1999 | Toledano | |
| 6,171,321 B1 | 1/2001 | Gifford et al. | |
| 6,428,550 B1 * | 8/2002 | Vargas et al. | 606/153 |
| 6,451,029 B1 | 9/2002 | Yeatman | |
| 6,485,496 B1 * | 11/2002 | Suyker et al. | 606/153 |
| 2003/0032967 A1 | 2/2003 | Park et al. | |
| 2003/0033000 A1 * | 2/2003 | DiCaprio et al. | 623/1.11 |
| 2003/0191482 A1 | 10/2003 | Suyker et al. | |
| 2005/0070934 A1 * | 3/2005 | Tanaka et al. | 606/153 |
| 2005/0119682 A1 * | 6/2005 | Nguyen et al. | 606/194 |

FOREIGN PATENT DOCUMENTS

| | | |
|---|---|---|
| EP | 1520531 | 4/2005 |
| WO | WO 2004/098417 | 11/2004 |

OTHER PUBLICATIONS

Office Action dated Jan. 4, 2006, for U.S. Appl. No. 10/675,497, filed Sep. 30, 2003.
European Search Report, dated Aug. 30, 2006, for EP Application No. 06252335.2.

* cited by examiner

*Primary Examiner*—Anhtuan T Nguyen
*Assistant Examiner*—Katherine M Dowe
(74) *Attorney, Agent, or Firm*—Frost Brown Todd LLC

(57) ABSTRACT

A surgical tool or applier for deploying an anastomotic ring that comprises a handle connected to an elongate shaft that terminates in an anastomotic ring deployment mechanism, which is moveable from an unactuated position to an actuated position. In order to prevent tissue from becoming trapped in the ring deployment mechanism during insertion or extraction of the tool, a sheath is adapted to cover ring deployment mechanism during insertion and extraction. The sheath is moveable with the ring deployment mechanism from the unactuated position to the actuated position. The sheath may comprise an elastomeric material, a braided thread, or another material.

15 Claims, 12 Drawing Sheets

SHEATH FOR ENABLING INSERTION AND EXTRACTION OF ANASTOMOTIC RING APPLIER

FIELD OF THE INVENTION

The present invention relates, in general, to surgery and, more particularly, to a device for performing a surgical procedure on the digestive system.

BACKGROUND OF THE INVENTION

The percentage of the world population suffering from morbid obesity is steadily increasing. Severely obese persons may be susceptible to increased risk of heart disease, stroke, diabetes, pulmonary disease, and accidents. Because of the effects of morbid obesity on the life of the patient, methods of treating morbid obesity have been the subject of intense research.

One known method for treating morbid obesity includes the use of anastomotic rings. Devices for applying anastomotic rings are known in the art. Devices of this nature are commonly adapted to insert a compressed anastomotic ring to an anastomotic opening formed between proximate gastrointestinal tissue walls. These applier devices may utilize a ring deployment mechanism comprising an expansion element that is actuated once the compressed ring is placed in the anastomotic opening, causing the anastomotic ring to expand from its compressed, cylindrically-shaped position to an actuated, hollow rivet-shaped position.

With some conventional anastomotic ring applier devices that use fingers or similar members to expand anastomotic rings, it may be possible for tissue to be trapped between the fingers of the applier device when it is inserted adjacent the proximate gastrointestinal tissue walls. Similarly, it may be possible for tissue to become trapped in the deployment mechanism during extraction of the device from the anastomosis site. The trapping of tissue between the fingers may result in undesirable consequences, such as pinching or tearing of the tissue, or even a compromise in the integrity of the anastomosis.

Some anastomotic ring applier devices known in the art incorporate a tubular sheath that is slideably located on the elongated shaft. The tubular sheath is typically in position over the ring deployment mechanism while the device is inserted adjacent the anastomosis site and during extraction of the device, and may be retracted to allow deployment of the ring. Thus, it may be desirable to have an anastomotic ring applier device that provides a reduced likelihood of tissue becoming trapped in the ring deployment mechanism of the device, yet does not necessarily require the time and a mechanism to retract a sheath from the fingers of the device.

BRIEF SUMMARY OF THE INVENTION

In one embodiment, an anastomotic ring applier device comprises a handle attached to an elongated shaft. The elongated shaft includes an anastomotic ring deployment mechanism. A sheath covers the ring deployment mechanism as it is inserted adjacent the anastomosis site and as it is extracted from the site, thereby preventing tissue from being trapped in the deployment mechanism. This embodiment does not require the surgeon to separately actuate the sheath and the ring deployment mechanism.

In another embodiment, an anastomotic ring applier device comprises a handle attached to an elongated shaft comprising a proximal portion and a distal portion. The distal portion of the elongated shaft includes a ring deployment mechanism. The ring deployment mechanism comprises a plurality of fingers that are moveable from an unactuated position in longitudinal alignment with the elongated shaft to a second position in which the fingers actuate outwardly from a longitudinal axis of the elongated shaft in order to actuate a portion of the anastomotic ring. The device further comprises a sheath that is adapted to cover the fingers of the ring deployment mechanism and that is adapted to move with the fingers from the first position in longitudinal alignment with the elongated shaft to the second position in which the fingers move out of longitudinal alignment with the shaft. Therefore, the device may prevent tissue from becoming trapped in the fingers of the ring deployment mechanism.

In yet another embodiment, an anastomotic ring applier device comprises a handle connected to a ring deployment mechanism by an elongated shaft. The ring deployment mechanism comprises a longitudinal end and a center portion. The device comprises an actuation mechanism that is adapted to move the longitudinal end of the ring deployment mechanism toward the center portion, thereby actuating a portion of the anastomotic ring. The applier device further comprises a sheath that is adapted to cover the longitudinal end of the ring deployment mechanism and that is adapted to move with the longitudinal end toward the center of the device. This may allow safe insertion and extraction of the device without adding sheath retraction steps to the process of deploying the anastomotic ring.

BRIEF DESCRIPTION OF THE FIGURES

The accompanying drawings, which are incorporated in and constitute a part of this specification, illustrate versions of the invention, and, together with the general description of the invention given above, and the detailed description of the versions given below, serve to explain the principles of the present invention.

DETAILED DESCRIPTION OF EMBODIMENTS OF THE INVENTION

Figure 1:
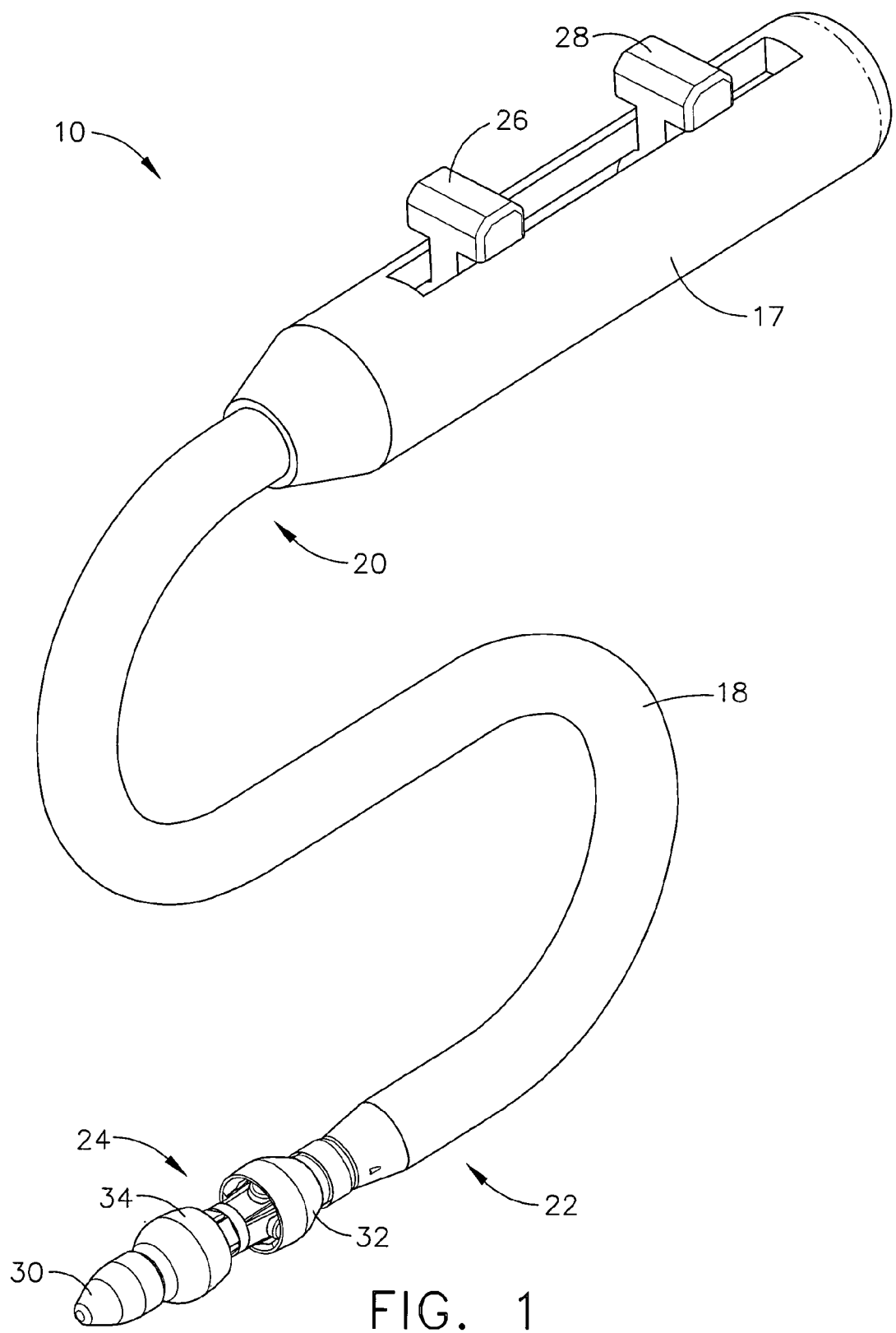
FIG. 1 is a perspective view of an anastomotic ring applier device.
Figure 2:
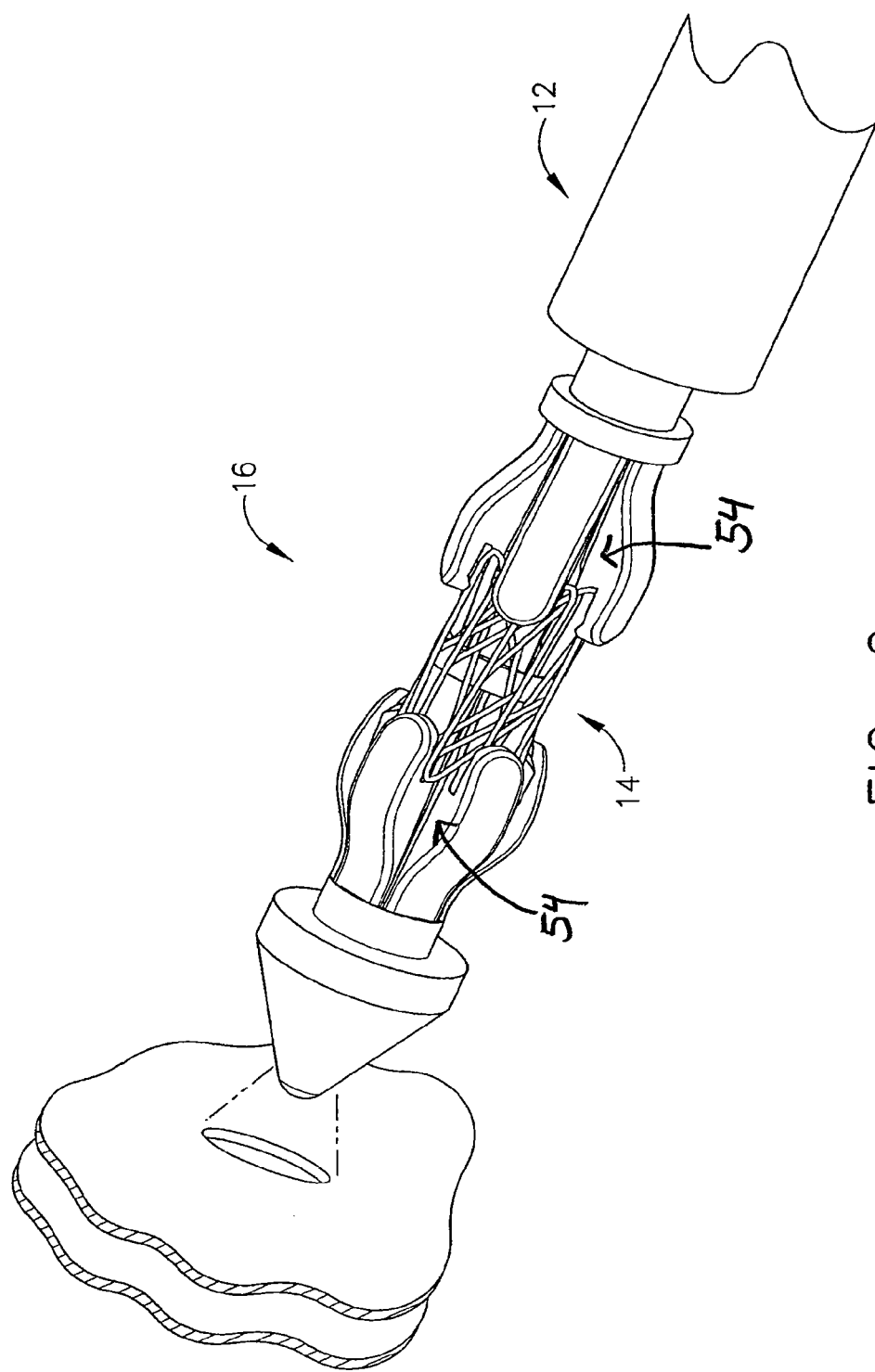
FIG. 2 is a partial perspective view of the distal portion of an anastomotic ring applier device holding an anastomotic ring in an unactuated position.
Figure 3:
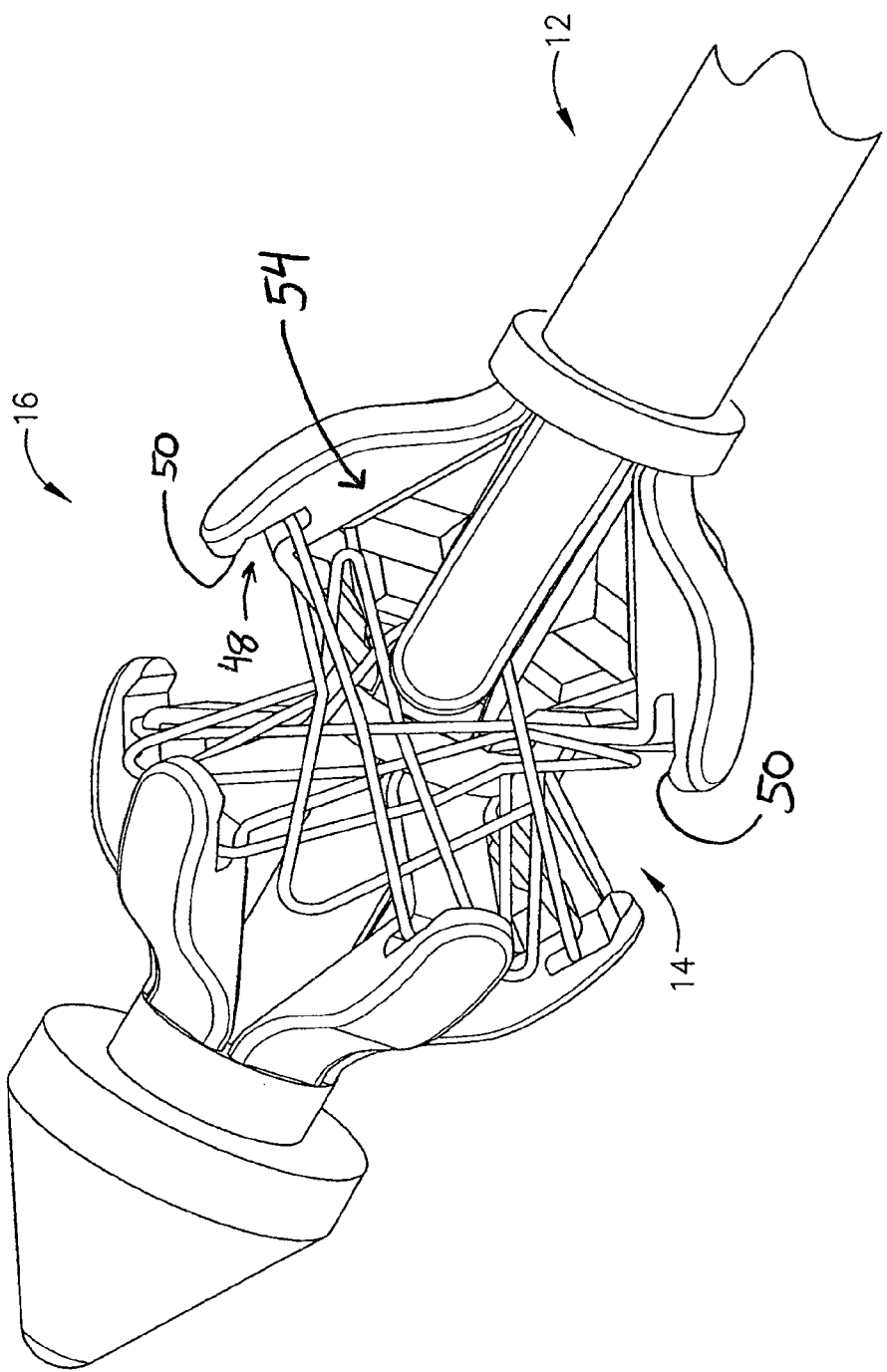
FIG. 3 is a partial perspective view of the distal portion of the device of FIG. 2 shown without a sheath holding an anastomotic ring in the actuated position.
Figure 4:
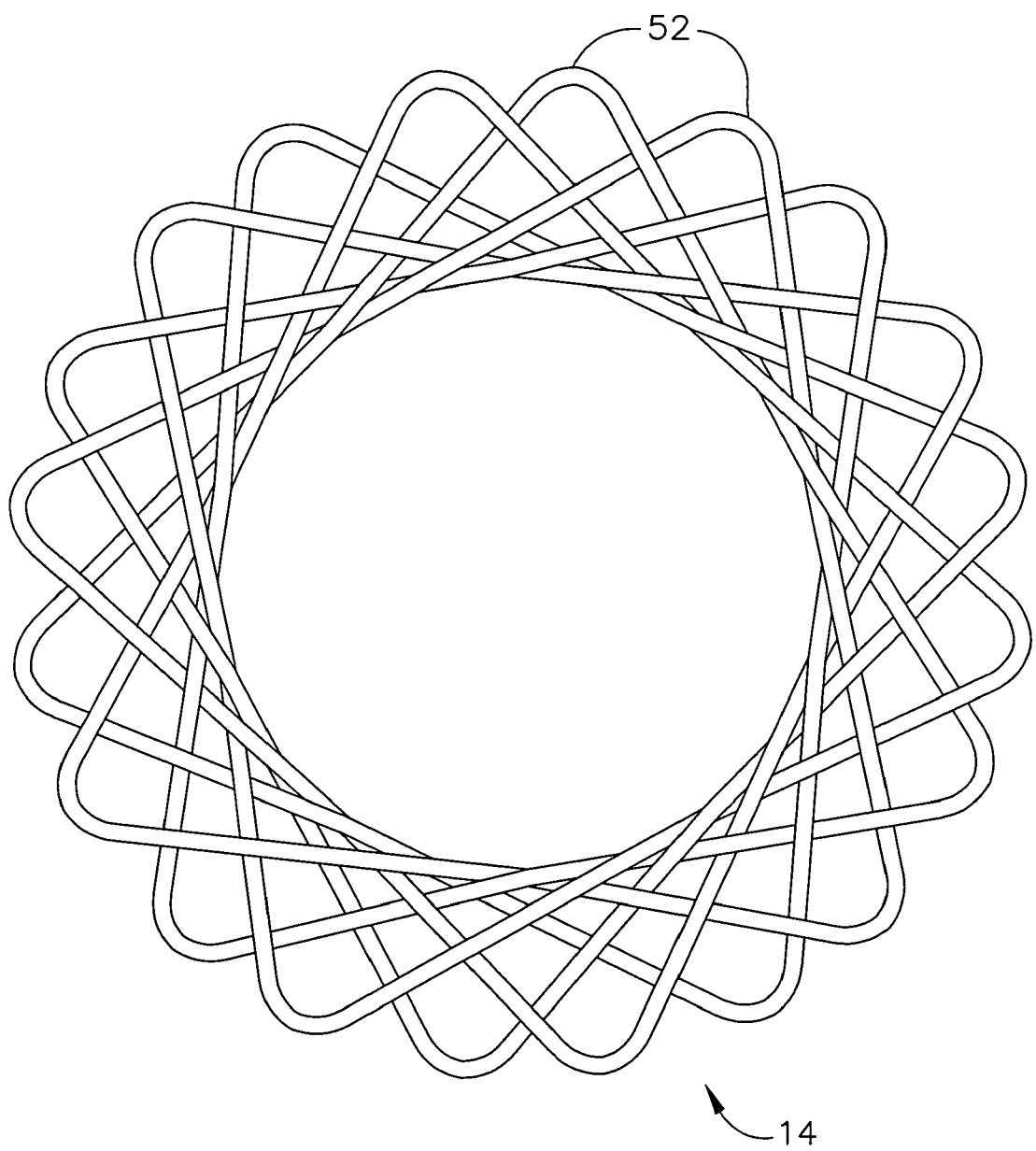
FIG. 4 is a frontal view of an actuated anastomotic ring.

Turning to the Drawings, wherein like numerals denote like components throughout the several views, FIG. 1 depicts an applier 10 that is operable to deploy and actuate an anastomotic ring device (not pictured in FIG. 1) from a generally cylindrical shape to one having properties of a hollow rivet, or ring, capable of forming an anastomotic attachment at an anastomosis target site, such as in a bariatric gastric bypass of a morbidly obese patient. FIG. 2 depicts another applier 12. It will be appreciated that appliers 10, 12 may be used in a variety of ways, including but not limited to laparoscopically or endoscopically. Applier 12 is shown in FIG. 2 with an anastomotic ring 14 on a deployment mechanism 16. In FIG. 2, anastomotic ring 14 is shown in the compressed, cylindrically-shaped position. In FIG. 3, deployment mechanism 16 of applier 12 has moved anastomotic ring 14 to the actuated, hollow rivet-shaped position. FIG. 4 is a close-up view of anastomotic ring 14 in the actuated position. Anastomotic ring 14 may comprise a shape memory effect (SME) material, such as nitinol by way of example only, that further assists in actuation to an engaging hollow rivet shape. Other suitable anastomotic ring 14 materials will be apparent to those of ordinary skill in the art. An exemplary anastomotic ring 14 is described in detail in U.S. Patent Application Publ. No. US 2003/0032967 to Park et al.

It will be appreciated that the terms "proximal" and "distal" are used herein with reference to a clinician gripping a handle of applier 10. It will be further appreciated that for convenience and clarity, spatial terms such as "right", "left", "vertical" and "horizontal" are used herein with respect to the drawings. However, surgical instruments are used in many orientations and positions, and these terms are not intended to be limiting and absolute. In addition, aspects of the invention have application to surgical procedures performed endoscopically and laparoscopically, as well as an open procedure or other procedures. Use herein of one of these or similar terms should not be construed to limit the present invention for use in only one category of surgical procedure.

Referring again to FIG. 1, applier 10 of the present example comprises a handle 17 connected to an elongated shaft 18 having a proximal end 20 and a distal end 22. As shown in FIG. 1, elongated shaft 18 is flexible, either along its entire length or at one or more joints. Of course, shaft 20 may alternatively be rigid, resilient, malleable, or have other properties. Distal end 22 of shaft 18 comprises a ring deployment mechanism 24. Deployment mechanism 24 may be actuated by a button or lever located on handle 17. As shown in FIG. 1, handle 17 comprises a pair of actuator members 26, 28. In the present example, actuator members 26, 28 comprise sliders. The functioning of exemplary actuator sliders 26, 28 will be described below. It will be appreciated, however, that actuator members 26, 28 may take a variety of other forms and have a variety of other functions.

In the present example, ring deployment mechanism 24 is located proximal to a tip 30. Applier 10 includes a feature to prevent tissue from becoming trapped in deployment mechanism 24 when applier 10 is inserted or extracted from the anastomosis site. In FIG. 1, a proximal sheath 32 and a distal sheath 34 are pictured.

Figure 7:
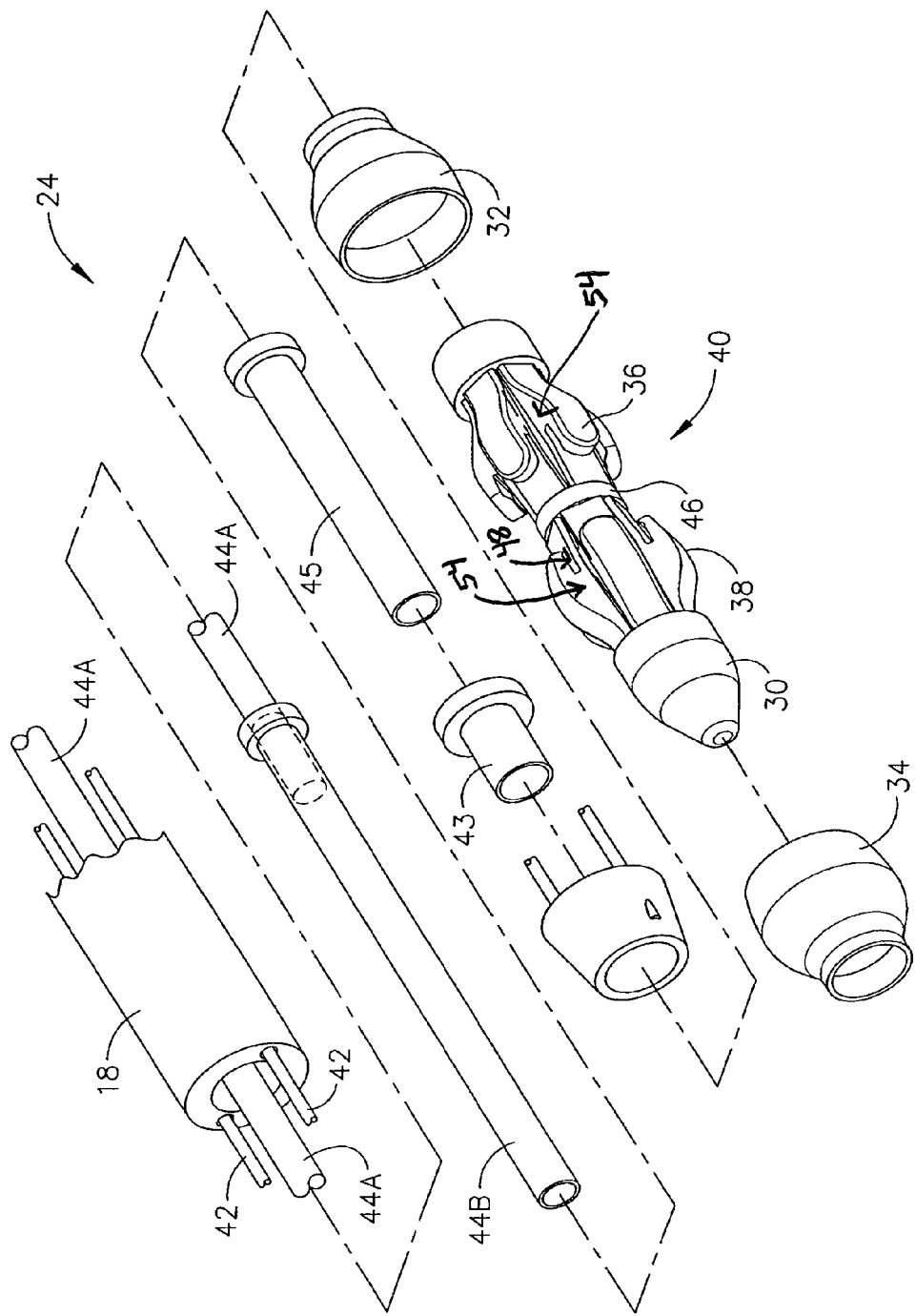
FIG. 7 is a perspective, exploded view of the anastomotic ring deployment mechanism of the device of FIG. 1.
Figure 12:
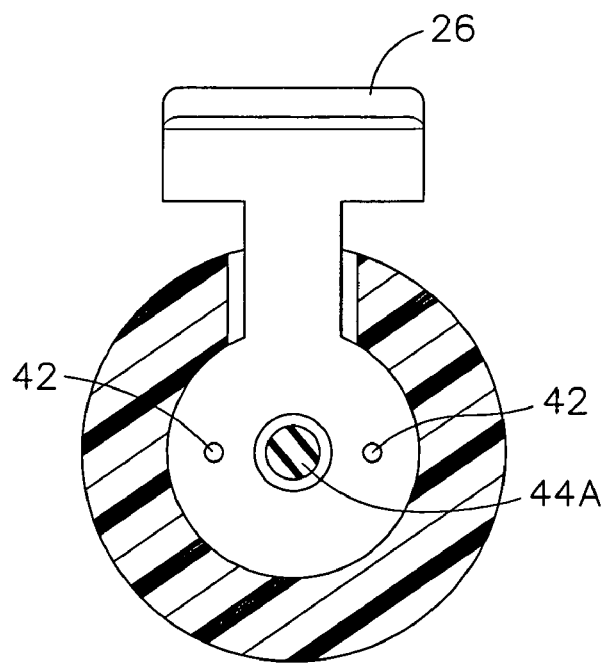
FIG. 12 is a cross-sectional view taken along Plane 12 of FIG. 11.
Figure 13:
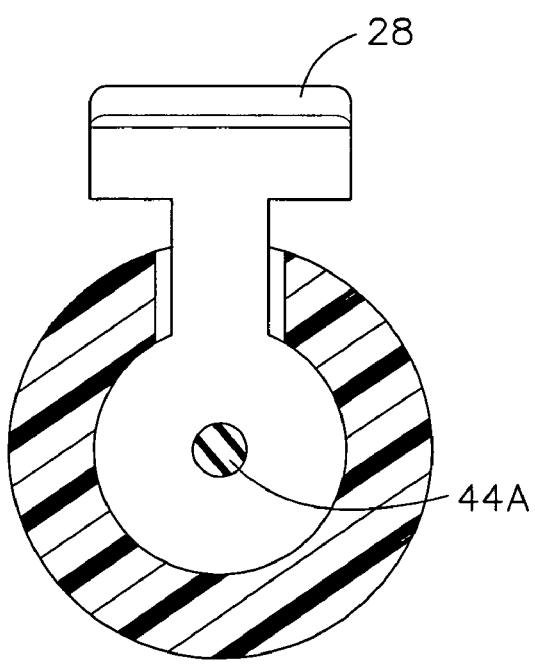
FIG. 13 is a cross-sectional view taken along Plane 13 of FIG. 11.

Referring to FIG. 7, ring deployment mechanism 24 of the present example is shown in an exploded perspective view, demonstrating how proximal sheath 32 fits over a plurality of proximal fingers 36, and distal sheath 34 fits over a plurality of distal fingers 38. Ring deployment mechanism 24 comprises a stationary molded actuation member 40. Of course, molded actuation member 40 may be formed using any suitable method other than molding. In the present example, molded actuation member 40 comprises proximal fingers 36 and distal fingers 38. Molded actuation member 40 also has central portion 46, which is fixedly connected to middle tube 45. Middle tube 45 fixed in distal end 22 of shaft 18. Proximal fingers 36 are connected to first actuator slider 26 via push/pull cables 42 of shaft 18 (FIG. 12). Push/pull cables 42 are in communication with an outer tube 43, which is fixedly connected with proximal fingers 36. Distal fingers 38 are connected to second actuator slider 28 via an inner tubes 44A, 44B of shaft 18 (FIG. 13). Inner tube 44A is fixedly connected with inner tube 44B. Proximal fingers 36 and distal fingers 38 are each in a double-hinged relationship with a central portion 46 of molded actuation member 40. Other suitable configurations for ring deployment mechanism 24 will be apparent to those of ordinary skill in the art.

Figure 8:
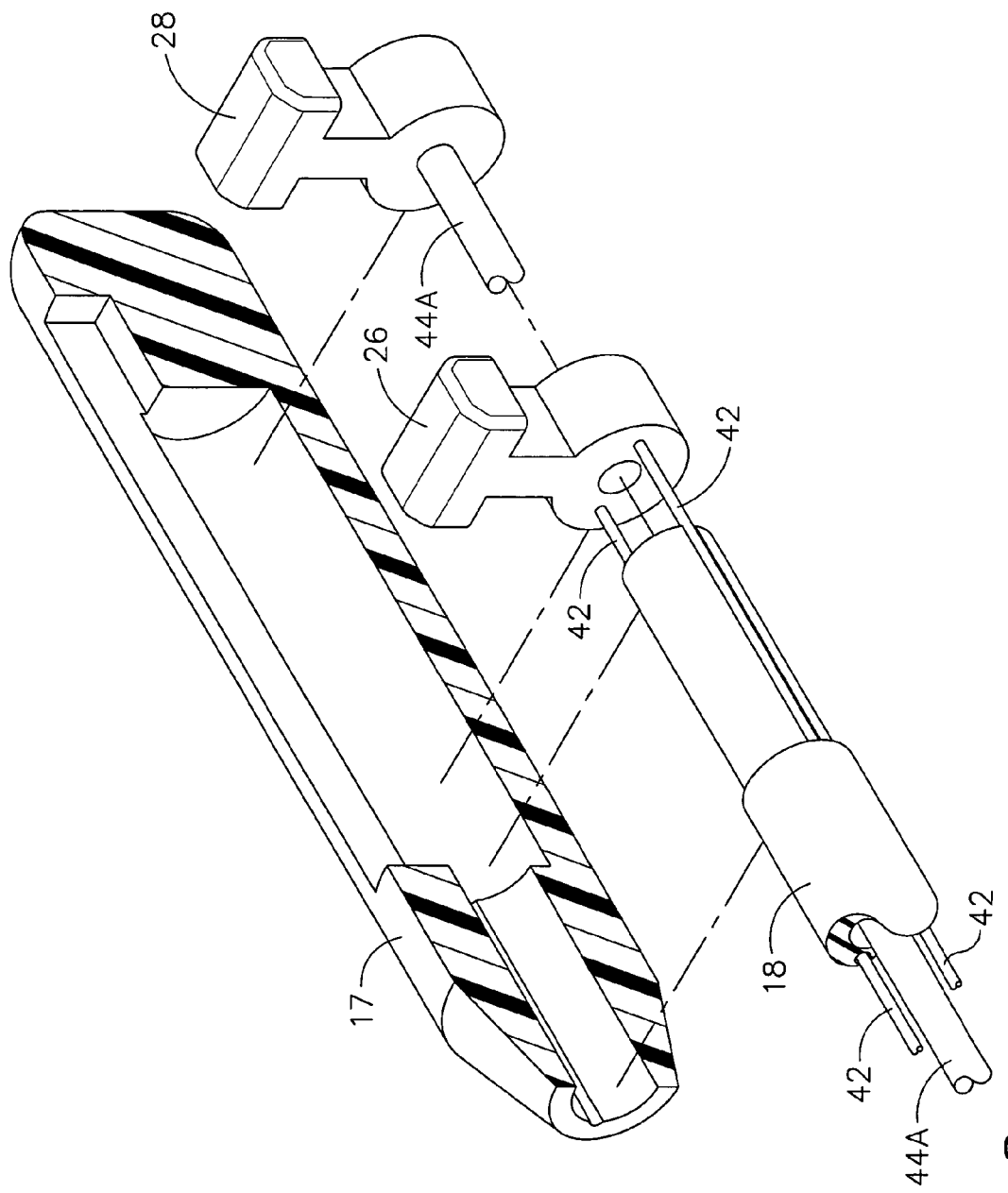
FIG. 8 is a perspective, cross-sectional exploded view of a proximal portion of the device of FIG. 1 with a left housing half omitted.
Figure 11:
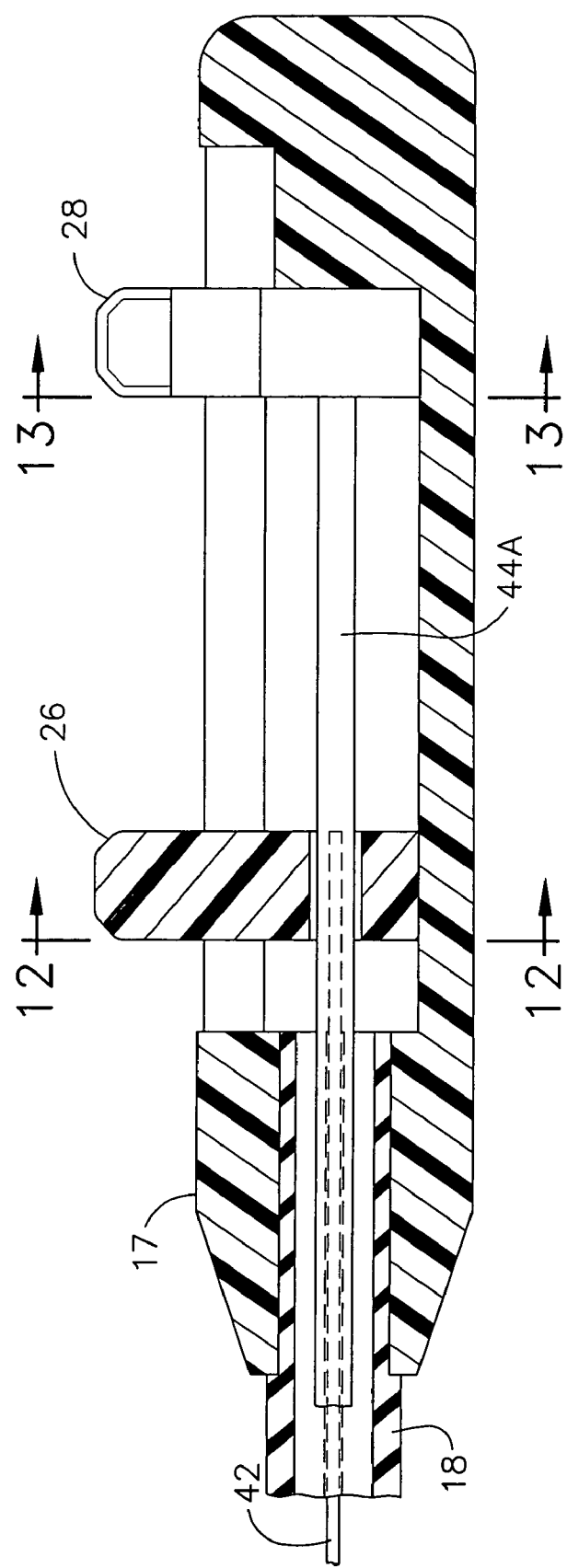
FIG. 11 is a partial cross-sectional view of a proximal portion of the device of FIG. 1.

FIGS. 8 and 11 show exemplary components of handle 17. In the present example, distal movement of first actuator slider 26 communicates distal motion to proximal fingers 36 via push/pull cables 42, thereby causing proximal fingers 36 to actuate outwardly in the manner of an umbrella due to their hinged relationship with central portion 46. Similarly, proximal movement of second actuator slider 28 communicates proximal motion to distal fingers 38 via inner tubes 44A, 44B, causing distal fingers 38 to actuate outwardly due to their hinged relationship with central portion 46. Thus, in this example, distal motion of first actuator slider 26 actuates a proximal portion of anastomotic ring 14 from the compressed position to the actuated position, while proximal motion of second actuator slider 28 actuates a distal portion of anastomotic ring 14 from the compressed position to the actuated position. In another embodiment, handle 17 is configured such that first actuator slider 26 is in communication with distal fingers 38, while second actuator slider 28 is in communication with proximal fingers 36. Suitable configurations for accomplishing such relationships will be apparent to those of ordinary skill in the art. Alternatively, any other suitable means, method, or mechanism for actuating an anastomotic ring from a compressed position to an actuated position may be used.

Fingers 36, 38 are configured to hold an anastomotic ring by engaging petals 52 prior to and during deployment of the anastomotic ring, and release petals 52 upon deployment of the anastomotic ring 14. Proximal fingers 36 and distal fingers 38 of the present example comprise gripping slots 48, each of which include an inwardly-directed retention tip 50. Gripping slots 48 may assist in retaining anastomotic ring 14 when it is in the compressed position, while retention tip 50 may allow anastomotic ring 14 to disengage from petals 52 of anastomotic ring 14 after it has been deployed in the actuated position. Other suitable configurations for fingers 36, 38 will be apparent to those of ordinary skill in the art.

Figure 5:
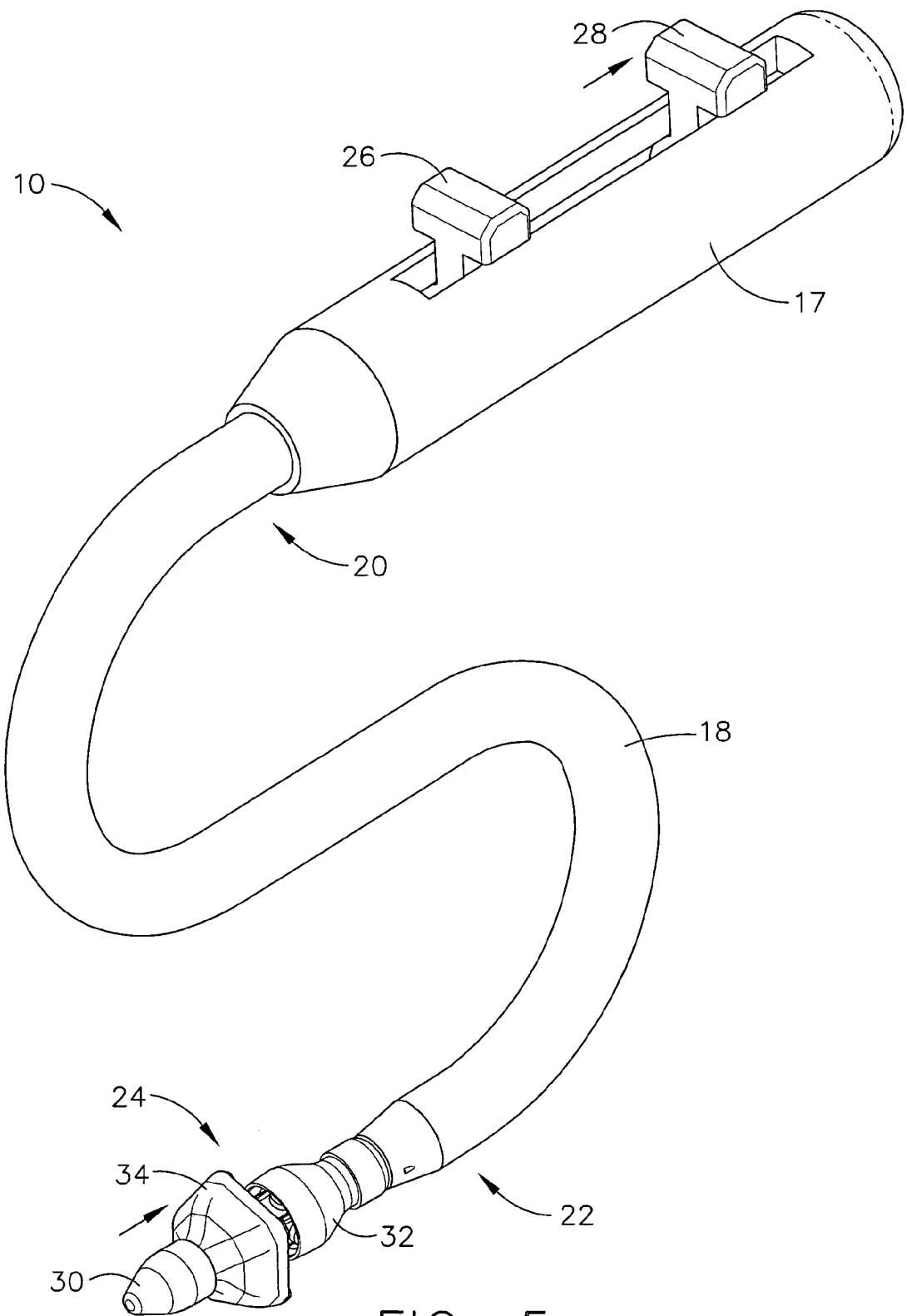
FIG. 5 is a perspective view of the anastomotic ring applier device of FIG. 1 with the distal portion of its ring deployment mechanism actuated.
Figure 6:
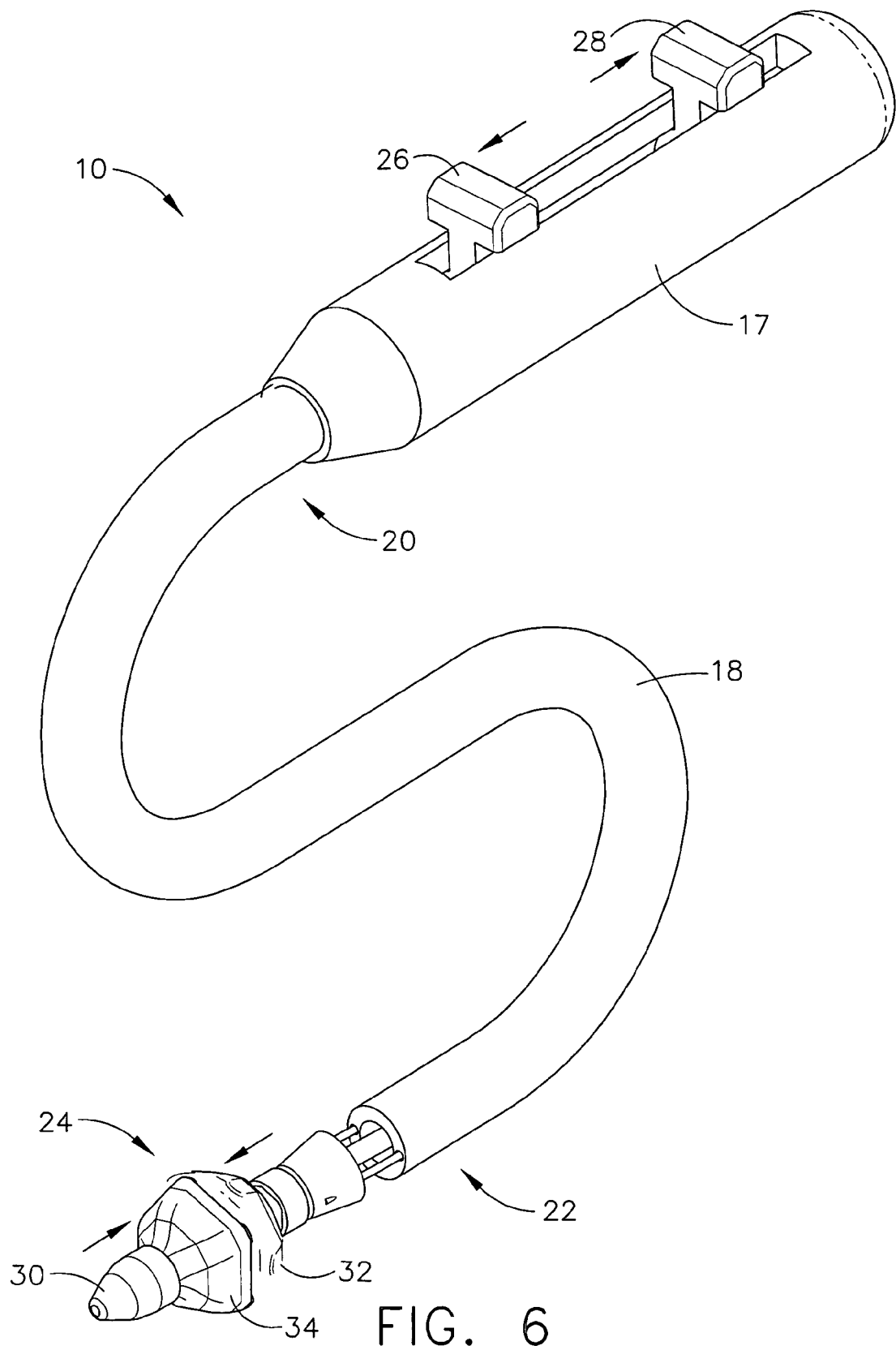
FIG. 6 is a perspective view of the device of FIG. 1 with both the distal portion and the proximal portion of its ring deployment mechanism actuated.

As shown in FIG. 7, ring deployment mechanism 24 includes gaps 54 between proximal fingers 36 and between distal fingers 38. Proximal sheath 32 is adapted to cover proximal fingers 36, and distal sheath 34 is adapted to cover distal fingers 38 in order to prevent tissue from becoming lodged in gaps 54 during insertion and extraction of applier 10. As shown in FIG. 5, distal sheath 34 is adapted to move to an actuated position along with distal fingers 38 in response to proximal movement by second actuator slider 28. This allows distal sheath 34 to prevent tissue from becoming trapped in gaps 54 during insertion or extraction of applier 10 without interfering with deployment of anastomotic ring 14 or requiring the surgeon to take the extra time and effort to retract the sheath. FIG. 6 shows both proximal fingers 36 and distal fingers 38 moved to the expanded position as a result of movement of actuator sliders 26, 28.

Proximal and distal sheaths 32, 34 may be affixed to proximal and distal fingers 36, 38, respectively, by an adhesive, such as glue, by mechanical fasteners, or any other suitable means or method. In one embodiment, proximal and distal sheaths 32, 34 comprise an elastomeric material that expands with proximal and distal fingers 36, 38, respectively. In another embodiment, proximal and distal sheaths 32, 34 are made of braided thread. Even if the thread material has no elasticity, it may dilate readily, ensuring coverage of gaps 54 while allowing fingers 36, 38 to move to the expanded position. Other suitable materials and configurations for sheaths 32, 34 will be apparent to those of ordinary skill in the art.

Figure 9:
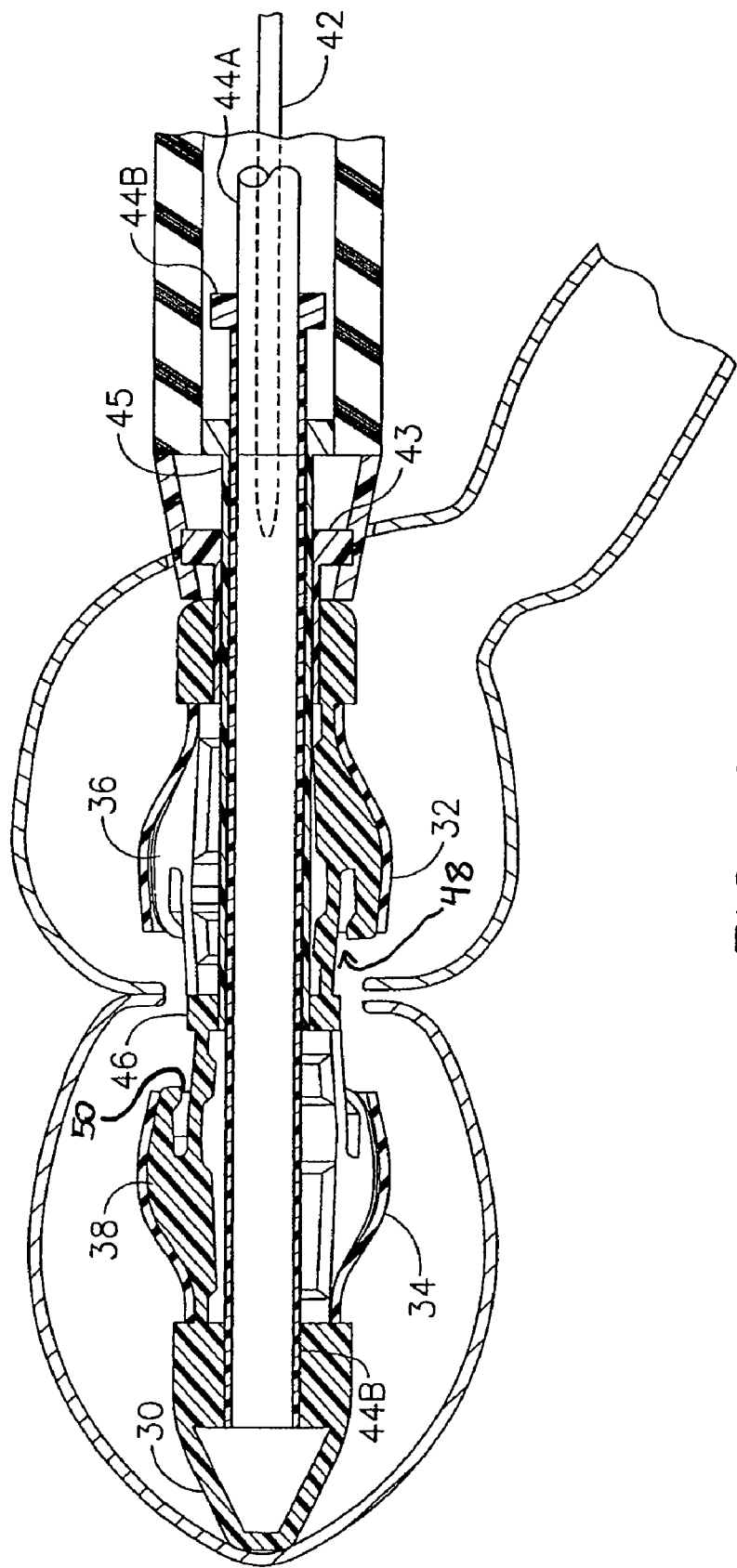
FIG. 9 is a partial cross-sectional view of the distal portion of the device of FIG. 1 inserted through an anastomotic opening.

In one example of operation, anastomotic ring 14 is held on ring deployment mechanism 24 by gripping slots 48 of proximal and distal fingers 36, 38. Applier 10 is inserted adjacent the anastomosis site, where an opening 56 is formed in two proximate gastrointestinal passages 58, 60, as shown in FIG. 9. As applier 10 is inserted, proximal and distal sheaths 32, 34 act to prevent tissue from becoming trapped in gaps 54. Of course, sheaths 32, 34 may serve a variety of other purposes.

Figure 10:
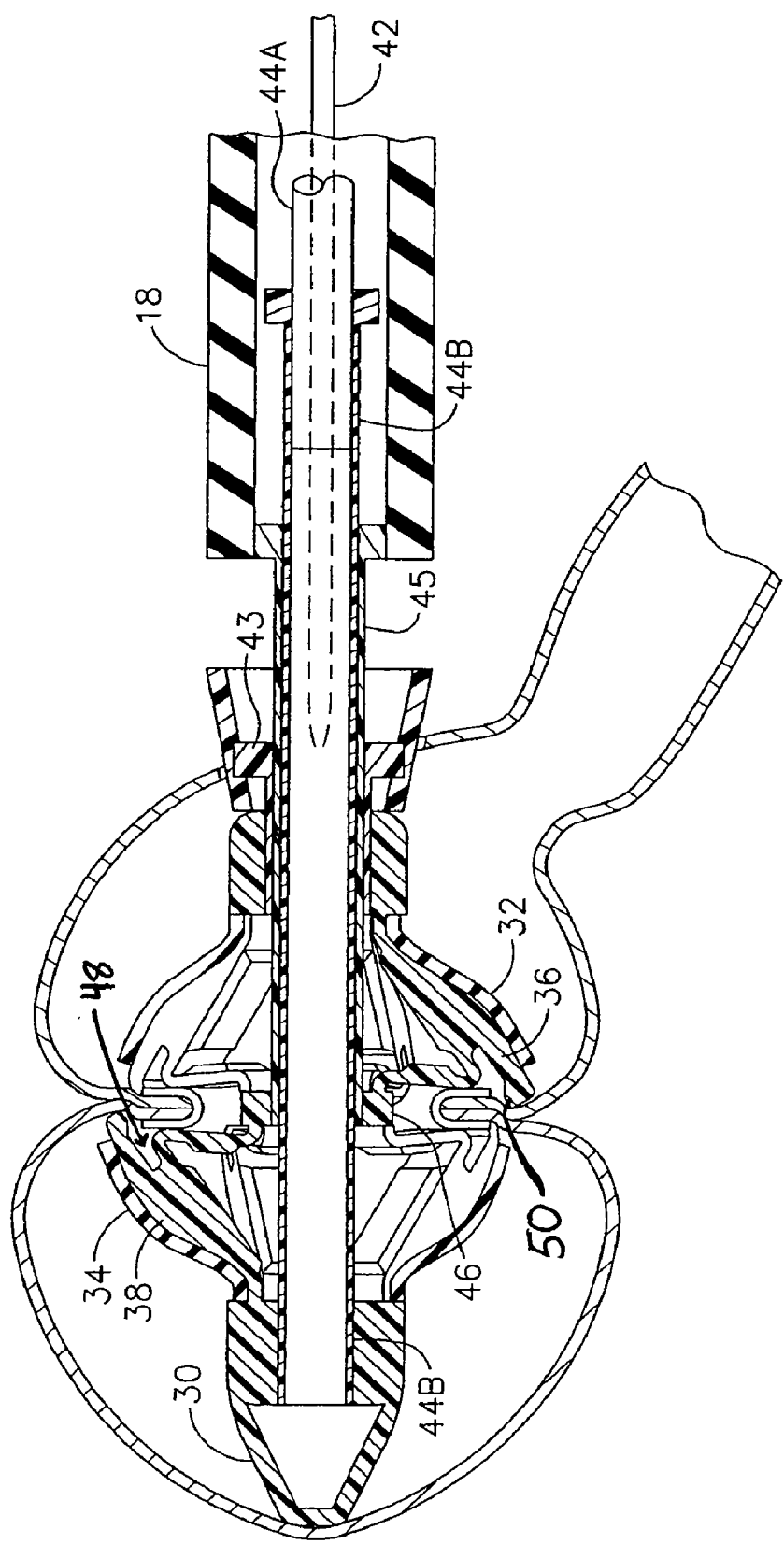
FIG. 10 is a partial cross-sectional view of the distal portion of the device of FIG. 1 forming an anastomotic attachment between proximate gastrointestinal tissue walls.

Referring now to FIG. 10, once ring deployment mechanism 24 is inserted into the anastomotic opening, first and second actuator sliders 26, 28 may be moved to their respective activated positions, causing fingers 36, 38 to actuate outwardly. This may expand anastomotic ring 14 from its compressed, cylindrical-shaped position to its actuated, hollow rivet-shaped position, forming an anastomotic attachment between the gastrointestinal tissue walls. Other applications and methods of operating applier 10 will be apparent to those of ordinary skill in the art.

Having shown and described various embodiments and concepts of the invention, further adaptations of the methods and systems described herein can be accomplished by appropriate modifications by one of ordinary skill in the art without departing from the scope of the invention. Several of such potential alternatives, modifications, and variations have been mentioned, and others will be apparent to those skilled in the art in light of the foregoing teachings. Accordingly, the invention is intended to embrace all such alternatives, modifications and variations as may fall within the spirit and scope of the appended claims and is understood not to be limited to the details of structure and operation shown and described in the specification and drawings. Additional advantages may readily appear to those skilled in the art.

What is claimed is:

1. A surgical instrument for implanting an anastomotic ring device, comprising:
   (i) a handle;
   (ii) a ring deployment mechanism configured to receive an anastomotic ring, wherein the ring deployment mechanism is adapted to move between an unactuated, generally cylindrical position and an actuated, hollow rivet-forming position, wherein the ring deployment mechanism comprises a plurality of distal fingers, a plurality of proximal fingers, and a central member positioned longitudinally between the plurality of distal fingers and the plurality of proximal fingers, wherein each distal finger comprises a proximal segment in a hinged relationship with a corresponding distal segment, wherein the proximal segment of each distal finger is further in a hinged relationship with the central member, wherein each proximal finger comprises a proximal segment in a hinged relationship with a corresponding distal segment, wherein the distal segment of each proximal finger is further in a hinged relationship with the central member, wherein the central member longitudinally separates the proximal segments of the distal fingers from the distal segments of the proximal fingers;
   (iii) an actuation mechanism for communicating actuating force to the ring-deployment mechanism, wherein the actuation mechanism comprises a first actuating slider and a second actuating slider, wherein the first actuating slider is in communication with the plurality of proximal fingers via a plurality of cables, wherein the second actuating slider is in communication with the plurality of distal fingers via a tube;
   (iv) an elongate shaft connecting the handle to the ring deployment mechanism and operatively configured to transfer the actuating force from the handle to the ring deployment mechanism, wherein the longitudinal position of the central member is fixed relative to the elongate shaft;
   (v) a first sheath adapted to cover the plurality of proximal fingers during insertion and extraction of the instrument, wherein the sheath is adapted to expand radially outwardly to move from the unactuated position to the actuated position along with the plurality of proximal fingers; and
   (vi) a second sheath adapted to cover the plurality of distal fingers during insertion and extraction of the instrument, wherein the sheath is adapted to expand radially outwardly to move from the unactuated position to the actuated position along with the plurality of distal fingers.

2. The surgical instrument of claim 1, wherein the first sheath and the second sheath respectively comprise an elastomeric polymer.

3. The surgical instrument of claim 1, wherein the first sheath and the second sheath respectively comprise a braided material.

4. The surgical instrument of claim 3, wherein the braided material is dilatable.

5. The surgical instrument of claim 1, wherein actuation of the first actuating slider moves both the plurality of proximal fingers and the first sheath from the unactuated position to the actuated position.

6. The surgical instrument of claim 1, wherein actuation of the second actuating slider moves both the plurality of distal fingers and the second sheath from the unactuated position to the actuated position.

7. The surgical instrument of claim 1, wherein the first sheath and the second sheath are respectively secured to the ring deployment mechanism by adhesive.

8. The surgical instrument of claim 1, wherein the first sheath and the second sheath are respectively press fit onto the ring deployment mechanism.

9. The surgical instrument of claim 1, wherein the first sheath and the second sheath respectively snap onto the ring deployment mechanism.

10. A surgical instrument for implanting an anastomotic ring, comprising:
    (i) a handle;
    (ii) an elongate shaft comprising a proximal portion and a distal portion, wherein said elongate shaft is attached to said handle adjacent the proximal portion of the elongate shaft;
    (iii) a ring deployment mechanism comprising a first longitudinal end, a second longitudinal end, and a center portion located on the distal portion of the elongate shaft, wherein the ring deployment mechanism is configured to receive a compressed anastomotic ring, wherein the ring deployment mechanism further comprises a plurality of distal fingers and a plurality of proximal fingers, wherein the center portion longitudinally separates the plurality of distal fingers from the plurality of proximal fingers, wherein the plurality of distal fingers are configured to move radially outward relative to the elongate shaft during actuation of the ring deployment mechanism, wherein the plurality of proximal fingers are configured to move radially outward relative to the elongate shaft during actuation of the ring deployment mechanism, wherein the plurality of distal fingers are located at the first longitudinal end of the ring deployment mechanism, wherein the plurality of proximal fingers are located at the second longitudinal end of the ring deployment mechanism;

(iv) an actuation mechanism for respectively moving the first longitudinal end and the second longitudinal end toward the center portion of the ring deployment mechanism to actuate a portion of the anastomotic ring, wherein the actuation mechanism comprises a first actuating slider and a second actuating slider, wherein the first actuating slider is in communication with the distal fingers via a tube, wherein the second actuating slider is in communication with the proximal fingers via a plurality of cables;

(v) a first sheath adapted to cover at least a portion of the first longitudinal end of the ring deployment mechanism during insertion and extraction of the instrument, wherein the sheath is adapted to move along with the first longitudinal end of the ring deployment mechanism, wherein the sheath is secured to the plurality of distal fingers, wherein the sheath is configured to move radially outward with the plurality of distal fingers during actuation of the first actuating slider, such that the sheath does not recede axially during actuation of the ring deployment mechanism; and (vi) a second sheath adapted to cover the second longitudinal end of the ring deployment mechanism, the sheath further being adapted to move along with the second longitudinal end of the ring deployment mechanism, wherein the second sheath is secured to the plurality of proximal fingers, wherein the second sheath is configured to move radially outward with the plurality of proximal fingers during actuation of the second actuating slider.

11. An instrument for implanting an anastomotic ring, the instrument comprising:

(i) a shaft having a distal end and a proximal end, the distal end having an axis defining longitudinal and radial directions;

(ii) a ring deployment mechanism positioned at the distal end of the shaft on the axis, the ring deployment mechanism having a plurality of members comprising a plurality of proximal members and a plurality of distal members, wherein the plurality of members are operable to be moved in the radial direction from a first position to a second position, wherein the first position corresponds to an unactuated position of an anastomotic ring, wherein the second position corresponds to an actuated position of an anastomotic ring, wherein each member of the plurality of members has a gripping slot, wherein each gripping slot of each member is configured to receive a respective petal of an anastomotic ring, wherein each gripping slot is oriented substantially parallel with the longitudinal axis of the shaft when the ring deployment mechanism is in the first position, wherein a first plurality of the gripping slots open proximally in a longitudinal direction when the ring deployment mechanism is in the first position, wherein a second plurality of the gripping slots open distally in a longitudinal direction when the ring deployment mechanism is in the first position;

(iii) an actuating mechanism in communication with the ring deployment mechanism, the actuating mechanism being operable to move the plurality of members from the first position to the second position, wherein the actuation mechanism comprises a first actuating slider and a second actuating slider, wherein the first actuating slider is in communication with the plurality of proximal members via a plurality of cables, wherein the second actuating slider is in communication with the plurality of distal members via a tube;

(iv) a first sheath adapted to cover the plurality of proximal members during insertion and extraction of the instrument, wherein the sheath is adapted to expand radially outwardly to move from the first position to the second position along with the plurality of proximal members; and (vi) a second sheath adapted to cover the plurality of distal members during insertion and extraction of the instrument, wherein the sheath is adapted to expand radially outwardly to move from the first position to the second position along with the plurality of distal members.

12. The instrument of claim 11, wherein movement of the first sheath and the second sheath is substantially constrained in the longitudinal direction.

13. The instrument of claim 11, wherein the first sheath and the second sheath respectively comprise at least one of a resilient material or a thread material.

14. The instrument of claim 11, wherein the plurality of members are further operable to be moved in the longitudinal direction.

15. The instrument of claim 11, wherein the first sheath and the second sheath are respectively configured to cover gaps defined by members of the plurality of members.

* * * * *